(12) United States Patent
Jay

(10) Patent No.: US 7,291,141 B2
(45) Date of Patent: Nov. 6, 2007

(54) METHOD AND APPARATUS FOR ENHANCING HAIR REMOVAL

(76) Inventor: Harvey H. Jay, 14 Cayuga Rd., Scarsdale, NY (US) 10583

(*) Notice: Subject to any disclaimer, the term of this patent is extended or adjusted under 35 U.S.C. 154(b) by 331 days.

(21) Appl. No.: 11/048,947

(22) Filed: Feb. 2, 2005

(65) Prior Publication Data

US 2006/0173447 A1 Aug. 3, 2006

(51) Int. Cl.
*A61B 18/18* (2006.01)
(52) U.S. Cl. .................. 606/9; 606/131; 128/898
(58) Field of Classification Search .............. 606/3, 606/9–13, 16–20, 22, 131, 133; 607/88–91; 128/898
See application file for complete search history.

(56) References Cited

U.S. PATENT DOCUMENTS

| | | | |
|---|---|---|---|
| 5,425,728 A | 6/1995 | Tankovich | |
| 5,595,568 A | 1/1997 | Anderson et al. | |
| 5,683,380 A | 11/1997 | Eckhouse et al. | |
| 5,735,844 A * | 4/1998 | Anderson et al. | 606/9 |
| 5,849,029 A | 12/1998 | Eckhouse et al. | |
| 5,885,273 A | 3/1999 | Eckhouse | |
| 6,050,990 A | 4/2000 | Tankovich et al. | |
| 6,063,076 A | 5/2000 | Mehl, Sr. et al. | |
| 6,152,917 A | 11/2000 | Tankovich | |
| 6,162,211 A | 12/2000 | Tankovich et al. | |
| 6,162,212 A | 12/2000 | Kreindel et al. | |
| 6,174,325 B1 | 1/2001 | Eckhouse | |
| 6,228,074 B1 * | 5/2001 | Almeida | 606/9 |
| 6,267,771 B1 | 7/2001 | Tankovich et al. | |
| 6,280,438 B1 | 8/2001 | Eckhouse et al. | |
| 6,383,176 B1 | 5/2002 | Connors et al. | |
| 6,387,089 B1 | 5/2002 | Kreindel et al. | |
| 6,406,474 B1 | 6/2002 | Neuberger et al. | |
| 6,595,986 B2 * | 7/2003 | Almeida | 606/9 |
| 6,676,655 B2 | 1/2004 | McDaniel | |
| 6,824,542 B2 * | 11/2004 | Jay | 606/9 |
| 2004/0034319 A1 | 2/2004 | Anderson et al. | |
| 2005/0177139 A1 * | 8/2005 | Yamazaki et al. | 606/9 |

FOREIGN PATENT DOCUMENTS

JP 2001-029124 * 2/2001

* cited by examiner

*Primary Examiner*—A. Farah
(74) *Attorney, Agent, or Firm*—R. Neil Sudol; Henry D. Coleman; William J. Sapone

(57) ABSTRACT

A method for removing hair from a skin surface includes removing protruding hair fibers from a skin surface in a plurality of temporally spaced treatment sessions by a process other than application of light energy. In each of the treatment sessions, one or more light pulses are applied to the skin surface to enhance the removal of hair by the process. The pulses are characterized by pulse parameters including radiation wavelength such that light of the pulses is absorbed by the hair fibers below the skin surface. The pulses are applied to the skin surface in the absence of an exogenous chromophore on the skin surface and the hair fibers along the skin surface. A hand held device includes a pulsed-light applicator and a cutting edge.

18 Claims, 1 Drawing Sheet

METHOD AND APPARATUS FOR ENHANCING HAIR REMOVAL

BACKGROUND OF THE INVENTION

This invention relates generally to a hair treatment process. More particularly, this invention relates to a method for the removal of hair.

As discussed in U.S. Pat. No. 6,280,438, hair may be removed from selected skin surfaces by the application of intense, wide area, pulsed electromagnetic (light) energy. According to the methodology of U.S. Pat. No. 6,280,438, the energy heats the hair and coagulates the tissue around the hair and follicle without damaging the healthy skin. Pursuant to that prior art disclosure, it is preferable to provide an optically transparent water based gel on the skin prior to treatment with the electromagnetic energy. The gel cools the epidermis but is applied so as not to enter the cavity around the hair follicle, and thus does not cool the hair and the hair follicle. The applied energy then coagulates the hair without damaging the skin.

U.S. Pat. No. 6,280,438 teaches the use of incoherent polychromatic radiation in a wavelength range that penetrates into the skin without being highly attenuated. It is indicated in the patent that wavelengths shorter than 550 nm are not useful because they will be highly attenuated before reaching the lower parts of the hair follicles. Instead, wavelengths in the range of 550 to 630 nm are heavily absorbed by blood and can therefore be used to coagulate the vessels that feed the hairs. Additionally, longer wavelengths, in the range of 600 to 1100 nm have a very good penetration into non-pigmented skin and can be used to couple to the melanin of the hair.

U.S. Pat. No. 5,885,273 discloses a method of removing hair that includes producing a plurality of pulses of incoherent electromagnetic energy, which is filtered in accordance with the color of the hair being removed. A flashlamp produces pulses having delays on the order of 0.1 msec to 100 msec, and an energy fluence on the order of 10 to 100 J/cm$^2$. Energy that has a wavelength of less than 500 nm or 600 nm and greater than 1300 nm is preferably filtered out. Light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel-covered epidermis and less than the cooling time of the hair and follicle. Specifically, a pulse length of 50 msec if a single pulse is used or a delay of 50 msec between the pulses if a pulse sequence is used are appropriate values.

In brief, the art using electromagnetic radiation such as pulses of incoherent light is intended to permanently remove hair from selected skin surfaces. The light pulses have parameters such as spectral dispersion, pulse duration and total energy that are selected to destroy the hair follicles in the selected skin area. Understandably, such methods carry a certain amount of risk that the skin may be damaged. Accordingly, the prior art methods of hair depilation are typically intended for use by trained cosmetologists and other professionals. The consuming public is left with few options in removing undesired hair.

OBJECTS OF THE INVENTION

An object of the present invention is to provide a new and novel method for hair removal.

A related object of the present invention is to provide a method for enhancing or improving hair removal, especially temporary hair removal.

More particularly, it is an object of the present invention to provide a method for enhancing or improving the results of temporary hair removal by other techniques, known or to be discovered, such as waxing, shaving, plucking, tweezing, or the using of depilatories.

A further object of the present invention is to provide such a method of hair treatment or removal that is safe for home use.

These and other objects of the present invention will be apparent from the drawings and descriptions herein. It is to be understood that each object of the invention is achieved by at least one embodiment of the invention. It is not necessarily the case that any embodiment achieves all of the objects of the invention.

SUMMARY OF THE INVENTION

The present invention is directed principally to a method wherein the application of pulsed light energy or electromagnetic radiation to a hair-bearing skin surface is used to enhance, facilitate, or improve the results of temporary hair removal by one or more different techniques including shaving, waxing, plucking, using depilatory creams, etc.

The light pulses may be applied before the removal of the protruding hair fibers by one or more of the non-light techniques, but preferably the light pulses are applied to the skin surface substantially during or after the removal of the protruding hair fibers. The absorption of light energy by the remaining portions of the hair fibers can produce one or more physical effects, that is, changes in one or more physical characteristics of the hair, that enhance, facilitate, or improve the result of temporary hair removal.

Some examples of such physical effects include (a) rounding-off or blunting the free ends of the remaining hair portions to prevent ingrown hair and to make the hairs feel softer or smoother upon their regrowth, (b) shortening the remaining portions of the hair fibers to delay the reappearance of the hair along the target skin surface, and (c) thinning the hair shafts to facilitate subsequent removal of the grown hair.

The present method is preferably used without the application of an exogenous chromophore. This simplifies the hair removal process.

The term "light energy" is used herein synonymously with the terms "irradiation" and "electromagnetic radiation" and "electromagnetic waveform energy."

A method for removing hair comprises, in accordance with the present invention, (a) applying one or more first pulses of light energy to a skin surface having protruding hair fibers, (b) removing the protruding hair fibers from the skin surface by a first process different from the application of light energy, within a first predetermined time after the applying of the pulses to the skin surface, (c) subsequently applying one or more second pulses of light to the skin surface, after the hair portions beneath the skin surface have grown and reappeared as protruding fibers along the skin surface, and (d) removing the protruding fibers from the skin surface by a second process different from the application of light energy, within a second predetermined time after the applying of the second pulses of light energy to the skin surface.

Pursuant to another feature of the present invention, the applying of the first pulses of light is carried out during a first hair treatment session and the applying of the second pulses of light is carried during a second treatment session temporally spaced from the first treatment session, the removing of protruding hair fibers by the first process taking place during the first treatment session and the removing of protruding hair fibers by the second process taking place during the second treatment session. Preferably, but not necessarily, the protruding hairs fibers are removed during the first treatment session within about one hour of the applying of the first pulses of light to the skin surface, while protruding hair fibers are removed during the second treatment session within about one hour of the applying of the second pulses of light.

The first process and the second process of hair removal may be the same process or different processes, for instance, waxing, shaving, plucking, tweezing, and using depilatory creams.

The pulses are characterized by pulse parameters including radiation wavelength such that light of the pulses is absorbed by the hair fibers to at least weaken the hair fibers, thereby facilitating removal of the hair fibers respectively by the first process and the second process.

A method for removing hair comprises, in accordance with the present invention, (i) removing protruding hair fibers from a skin surface by a first process other than an application of light energy to the skin surface, and (ii) after the removing of the protruding hair fibers or contemporaneously therewith, and prior to a reappearance of protruding hair on the skin surface, applying one or more first pulses of light to the skin surface, the applying of the pulses of light being carried out in the absence of an exogenous chromophore whether on the skin surface or in or surrounding the hair fibers at or below the skin surface. This method also comprises (iii) after the applying of the first pulses to the skin surface and after a reappearance of protruding hair fibers along the skin surface, removing the protruding hair fibers from the skin surface by a second process other than an application of light energy to the skin surface, and (iv) after the removing of the protruding hair fibers by the second process or contemporaneously (or substantially simultaneously) therewith, applying one or more second pulses of light to the skin surface, the applying of the second pulses of light being carried out in the absence of an exogenous chromophore whether on the skin surface or in or surrounding the hair fibers at or below the skin surface.

In a preferred embodiment, the applying of the first pulses of light in this method is carried out during a first hair treatment session and the applying of the second pulses of light is carried during a second treatment session temporally spaced from the first treatment session, the removing of protruding hair fibers by the first process taking place during the first treatment session and the removing of protruding hair fibers by the second process taking place during the second treatment session. It is contemplated that the treatment sessions are no more than about one hour in length. Of course, longer sessions are possible, for instance, in a spa setting.

The first process and the second process of hair removal in this method may be the same process or different processes, for instance, waxing, shaving, plucking, tweezing, and using depilatory creams.

The first pulses and the second pulses of this hair removal method are characterized by pulse parameters including radiation wavelength such that light of the first pulses and the second pulses is absorbed by the hair fibers to at least delay a reappearance of the hair fibers on the skin surface. In addition, the pulse parameters may be such that light of the first pulses and the second pulses is absorbed by the hair fibers to blunt free ends of remaining portions of the hair fibers, thereby reducing the chances that the hair will subsequently become ingrown.

A method for removing hair from a skin surface comprises, in accordance with the present invention, removing protruding hair fibers from a skin surface in a plurality of temporally spaced treatment sessions by a process other than an application of light energy. In each of the treatment sessions, one or more light pulses are applied to the skin surface to enhance the removal of hair by the process. The pulses are characterized by pulse parameters including radiation wavelength such that light of the pulses is absorbed by the hair fibers below the skin surface. The pulses are applied to the skin surface in the absence of an exogenous chromophore whether on the skin surface or in or surrounding the hair fibers at or below the skin surface.

A device for removing hair comprises, in accordance with the present invention, a hand-held casing; a light-pulse generator operatively connected to the casing; light guide componentry disposed on the casing and operatively connected to the light-pulse generator for directing light pulses to a skin surface; and at least one cutting edge or blade mounted to the casing for severing protruding hair along the skin surface, the pulses being characterized by pulse parameters including radiation wavelength such that light of the pulses is absorbed by the hair fibers below the skin surface.

The light used in a hair treatment method in accordance with the present invention may be incoherent and produced by a flashlamp or other source of incoherent electromagnetic radiation. Alternatively, the light may be coherent and produced by a laser source. In the former case the electromagnetic spectrum of the light pulses is a band of wavelengths, while in the latter case, the electromagnetic spectrum of a light pulse delivered at one time is a single wavelength. In the former case filters may be used to limit the band of transmitted wavelengths, while in the latter case the laser source may be adjustable or tunable for producing wavelengths of different frequencies. In any event, the light energy applied includes at least one wavelength absorbable by an endogenous chromophore in the hair such as eumelanin or pheomelanin.

A hair removal method in accordance with the present invention includes (a) generating a predetermined number of pulses of light each having a predetermined electromagnetic spectrum including at least one wavelength absorbable by an endogenous chromophore in a person's hair and (b) applying the pulses of light to a given skin surface that is free of exogenous chromophores, the pulses having at least one predetermined pulse duration, at least one predetermined inter-pulse interval (if the number of pulses is greater than one), and a predetermined total energy. The various pulse parameters are "predetermined" insofar as they are set or selected prior to the application of the light energy to the selected skin surface. The determination of the different pulse parameters is generally made partially at the time of manufacture of the light-generating device and partially by the selection or selections made by the user. Where the light pulses are applied to the skin surface after hair removal has been effectuated, the application of the pulses delays the appearance of visible hair fibers on the skin surface. This light-induced delay is beyond the delay that normally occurs using the particular non-light hair removal process.

Pursuant to the present method, light may be applied before, during, and/or after the removal of the hair fibers using a process other than the application of light energy. Where the application of light energy is prior to the hair removal, light absorption by the individual hair shafts tends to weaken the hair fibers and facilitate removal by the application of a shearing force (blade shaving) or a tensile force (plucking, tweezing) or the application of a chemical denaturing agent (depilatory).

The pulse parameters may vary from treatment session to treatment session. Where pulsed light energy is applied to a target skin surface in different passes during the same treatment session, one or more of the pulse-defining parameters (pulse duration, inter-pulse interval, light intensity, pulse number, total energy) may be varied from one pass to the next. The different passes may take place at different times relative to the hair removal, for example, one pass before hair removal and one pass after hair removal or one pass during hair removal and one pass after hair removal. Alternatively, the hair treatment method may encompass multiple passes before hair removal or multiple passes after hair removal, and/or multiple passes during hair removal.

The application of light energy contemporaneously or substantially simultaneously with the non-light removal of the hair means generally that the light is applied during the stroke or motion that results in the removal of the hair. This may be accomplished in the case of a blade by mounting a light source or applicator directly to the blade holder or casing.

The present invention also contemplates that light energy alone may be used in some hair treatment sessions, without non-light instrumentalities. Light pulses may be reapplied in a separate treatment session, for instance, prior to hair reappearance to further delay the time that the hair will appear on the skin surface after the hair has been removed. This preemptive light treatment may be undertaken without precise knowledge of when the hair may reappear. Alternatively, as discussed in detail hereinafter, the light may be applied preemptively before the expected appearance of regrown hair after a waiting period, as determined by counting days between one application of light and a subsequent appearance of light on the treated skin surface. This waiting period after the application of light arises from the partial or complete subdermal destruction of hair fibers at a distance below the skin surface. The greater the distance, the longer it takes for the hair to penetrate again to the skin surface.

As mentioned above, passing days may be counted between the applying of light pulses to a skin surface and a subsequent reappearance of hair fibers on the skin surface, thereby determining an expected hair regeneration period. After determination of this hair regeneration period, the same pulse sequence may be generated, having the same pulse number, the same electromagnetic spectrum(s), the same pulse duration(s), the same inter-pulse interval(s) (if applicable), and the same total energy. This pulse sequence is directed towards the given skin surface. Thereafter, prior to a lapse of the determined hair regeneration period, the light application may be repeated with pulses of light having (if desired) the same spectrum, the same number, the same duration, the same inter-pulse interval (if applicable), and the same total energy. It is to be noted that the hair regeneration period may lengthen with time, in part as a result of the light treatments. In recognition of that potentiality, the regeneration time may be recalculated after any given number of treatments. And if the regeneration time does increase, the interval between successive light treatments may be increased accordingly.

The present invention is directed chiefly to a method wherein light pulses are applied to a skin surface to enhance or improve the action of one or more non-light processes of hair removal. In addition, the present method contemplates hair treatment sessions using light along for extending the time until protruding hairs are again removed from the skin surface, exemplarily by a combination of light pulses and a non-light modality. The light pulses facilitate, augment, or improve the effect or action of the non-light modality or instrumentality on the removal of hair. This method may serve to maintain a smooth and hair free skin surface for an extended period between hair treatment sessions in which protruding hair fibers are eliminated.

The light treatment method of the present invention affects hair parameters including growth rate. Also, depending on the individual's genetics, the location of the hair treated, and the selected treatment parameters, the user's hair may experience changes in thickness, density, and color. More specifically, in many individuals, hair is likely to become finer, less dense, and lighter in color.

The method of the present invention may be applied to facial hair, leg hair, underarm hair, chest hair, etc., using hand held devices of prior art designs, for instance, with a light source such as a flashlamp, a reflector, one or more lenses, and an application interface such as a skin-contacting crystal. The crystal may function as a cooling element. Alternatively, a separate cooling medium such as a gel may be applied to the skin surface prior to the light application. Alternatively, where the applied energy is particularly low, and more specifically where the rate of energy application is low, it may be unnecessary to cool the skin surface.

Accordingly, the present invention contemplates the use of a hand held device for generating a predetermined number of pulses of light having a predetermined electromagnetic spectrum including at least one wavelength absorbable by an endogenous chromophore in a person's hair and for applying the pulses of light to a skin surface free of exogenous chromophores and having hair containing the endogenous chromophore, the pulses having one or more predetermined durations, one or more predetermined inter-pulse intervals (if number of pulses is greater than one), and a predetermined total energy. The light treatments are all performed without application of exogenous chromophores for light absorption purposes. The enhancement of hair removal, e.g., the retardation of hair growth, is effectuated through light absorption solely by endogenous chromophores such as melanin.

The inter-pulse interval (where the number of pulses is greater than one) may, in different applications of the invention, be anywhere from 1 microsecond to 2 seconds. Generally, the smaller the inter-pulse interval, the greater the risk of damage to the skin. Thus, the smaller inter-pulse intervals should be used only in professional settings. In home-based embodiments of the invention, the inter-pulse interval of a light treatment is preferably greater than 200 msec. An inter-pulse interval of such a magnitude allows partial cooling of the hair follicles and reduces the chances of complete follicle destruction and inadvertent damage to the epidermis. Preferably, the inter-pulse interval is between 200 msec and about 500 msec. An inter-pulse interval of 300 msec is effective.

The total energy applied may be anywhere from a micro-Joule per square centimeter of treated skin surface to about 200 J/cm$^2$. Generally, the higher energies entail greater risk to skin integrity and should be used only by skilled professionals. For home use, the total energy applied should be lower, between approximately 0.1 micro-Joule per cm$^2$ and approximately 40 J/cm$^2$ of the skin surface. This energy range is appropriate for persons of light skin color. Where the skin color is on the dark side, the upper limit of the total energy applied to a unit of skin surface should be less, for instance, approximately 20 J/cm$^2$.

Generally, it is contemplated that devices used in a method pursuant to the present invention will require a selection of a maximum or total energy to be applied to a skin surface. This requirement typically entails some restriction on the user's freedom in selecting the magnitudes of other pulse parameters. In a simple device, the user may be able to select only one pulse parameter, namely the total energy. Such a device might, for instance, have high, medium and low settings. In a more complex device, setting of the total energy applied by a pulse sequence will limit the range of options available to the user in setting the other parameters. For instance, once the user selects the total energy and the pulse duration, the number of pulses is determined, provided that the rate of energy production or intensity is not adjustable. If the intensity is adjustable, the user will have some leeway in selecting both the pulse duration and the number of pulses. In that case, the intensity may be automatically controlled by the light-generating device so that the total energy does not exceed the set value.

The duration of the light bursts or pulses may be as little as 1 micro-second or as great as two seconds. The shortest durations and higher energies are recommended for professionally supervised light treatments only. For ordinary consumers or unskilled users, the pulse duration should be longer, preferably above approximately 6 msec and more preferably between approximately 6 msec and approximately 20 msec. A pulse duration of 7 msec is effective.

Pursuant to one embodiment of the present invention, the light of the pulses is incoherent and the spectrum includes wavelengths between about 300 nm and 1200 nm. Longer wavelengths are used for darker skin, for deeper hair fibers and deeper impact on the hair. In some embodiments of the invention, the spectrum of the pulses may be limited to wavelengths between about 300 nm and 550 nm. These embodiments will require a more frequent application of the light energy to effectuate temporary hair removal. However, because of the retardation of hair growth, the frequency of light application required to maintain a hair free skin surface will generally decrease with use.

The number of pulses in each pulse sequence or treatment session (as applied to a given skin area) may be between one and ten, while the total duration of a pulse sequence ranges between 1 microsecond and 38 seconds.

As indicated above, the present invention contemplates that some adjustment may be made by the user in the particular operational parameters of the light application device. For instance, a simple hand-held device may have a plurality of settings, for instance, high, medium, and low, where one or more of the operational parameters have different pre-established values depending on the setting. Thus, high, medium, and low settings may vary in the number of applied pulses, the pulse duration, the inter-pulse interval, and/or the total energy applied. A user could start with a low setting to see whether there is a positive effect and if not, try the next higher setting. Usually, it is preferable to use the lowest setting which accomplishes the desired result.

It is to be noted that consumer devices may be preprogrammed with automatically operating safety controls which inhibit the user from inadvertently exposing himself or herself to dangerous quantities of light energy. Thus, in a relatively complex consumer product, the user's setting of one parameter at a potentially dangerous value will cause the device either to limit the selectable ranges of one or more other pulse parameters or to automatically adjust pulse parameters to prevent an excessive rate of energy delivery. For instance, the selection of a small inter-pulse interval may prevent the user from selecting a long pulse duration and/or a small number of pulses or, alternatively, may result in an automatic diminution of the intensity (e.g., via engagement of an intensity-reducing filter).

The present invention provides a method especially for the temporary removal of hair. The method is safe for home use. The pulsed-light energies used are sufficiently low to avoid skin damage. Because the light may be applied prior to the appearance of hair on a skin surface, the skin surface may be maintained in a hairless condition continuously. If the individual wishes to grow hair at any location, this is possible by merely refraining from light application. The present invention contemplates the use of a light applicator together with a more conventional form of hair removal. Optionally, the light pulses may be applied alone in other treatment sessions, without another hair removal process, before hair reappears. This stand-alone light-based hair treatment may be undertaken periodically, say, at intervals of a week to a few months. In some cases, the light application may be daily, as a substitute for daily shaving with a razor or shaver.

It should be understood that the present methodology may be used in professional settings, in spas or salons, by professional cosmetic service providers. Higher energies may be used in such settings. Even higher energies and more complex settings may be used by licensed medical professionals in medical offices.

DETAILED DESCRIPTION OF THE PREFERRED EMBODIMENTS

Figure 1:
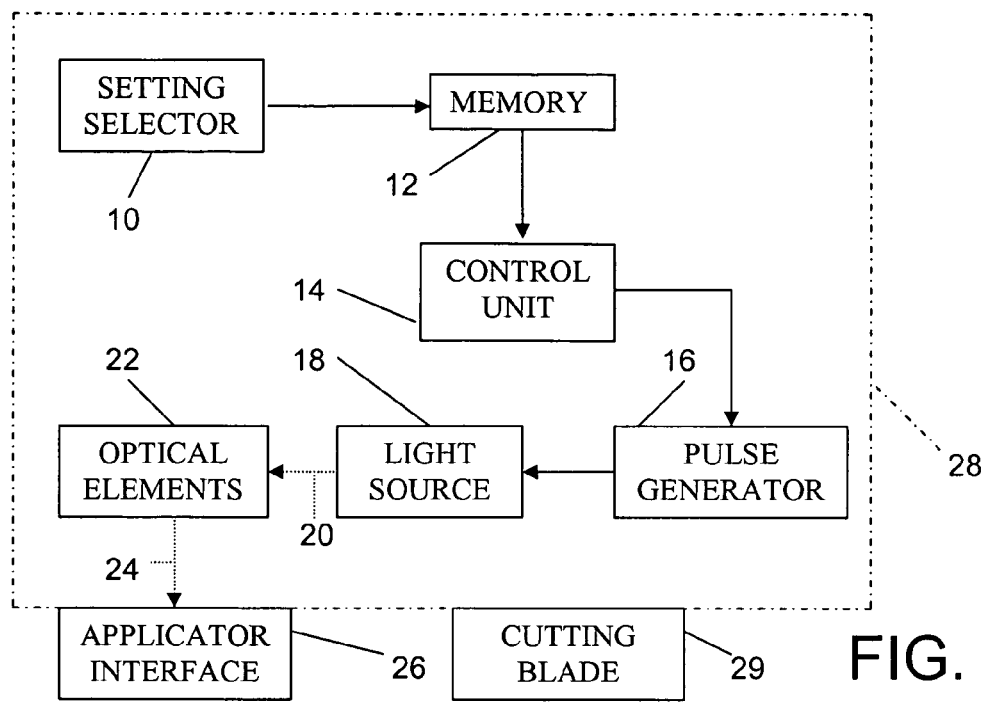
FIG. 1 is a block diagram of a light-pulse generating device for use in a method in accordance with the present invention.

As depicted in FIG. 1, a device for generating light pulses for application to a skin surface in a hair treatment process includes a manually operable setting selector 10 connected at an output to a memory 12 in turn connected at an output to a control unit 14. Memory 12 stores pre-established combinations of light pulse parameters including pulse width or duration, inter-pulse interval or delay time, pulse number, light intensity, and total treatment energy. Control unit 14 may be a microprocessor or a special logic circuit connected to a pulse generator 16 for inducing the generator to produce a sequence of electrical control pulses fed to a source 18 of incoherent light energy. Source 18 produces light with a spectral distribution including wavelengths between 500 nm and 1200 nm. Control unit 14 may be connected directly to source 18 where the source incorporates means for varying pulse parameters pursuant to encoded instructions.

Light source 18 (as well as the entire light pulse applicator) may take any known form such as those disclosed in U.S. Pat. No. 6,280,438 and U.S. Pat. No. 5,885,273. Thus, light source 18 may be a Xenon flashlamp.

Light 20 generated by source 18 is directed through an array of optical elements 22 that may include one or more reflectors, lenses, and filters (not separately shown). Where an adjustable filter is included, control unit 14 may be connected to the filter for operatively modifying the action thereof. For instance, in the case of an adjustable neutral density filter, control unit 14 may induce a change in the filter density to control the intensity, and therefore the power, of the light applied to a selected skin surface.

In the case of multiple wavelengths of light being produced, an adjustable filter may be included in the optical elements 22 and/or the applicator interface 26. These filters can block undesired wavelengths and allow desired wavelengths to pass. Low end filters that block lower or shorter wavelengths, high end filters that block higher or longer wavelengths or band pass filters that block some high or some low end wavelengths may be utilized.

Light 24 leaving the optical array 22 is delivered or applied to a skin surface via an applicator or interface element 26 exemplarily taking the form of a crystal. U.S. Pat. No. 6,280,438 and U.S. Pat. No. 5,885,273 disclose kinds of applicators or interfaces utilizable in the device of FIG. 1 (or 2). Applicator or interface element 26 may function in part to cool the skin surface prior to, during, and/or after a light application procedure. Cooling may be accomplished, if necessary, by using a crystal-type applicator or interface 26, with or without a layer of gel, as described in U.S. Pat. No. 6,280,438 and U.S. Pat. No. 5,885,273. Alternatively or additionally, cooling may be accomplished by spraying a coolant on the skin surface or by blowing air or other gas on the skin surface. In the former case, the light application device is provided with a reservoir of coolant fluid, an ejection mechanism or pump and a nozzle. In the latter case, the device is provided with a pump or compressor and a nozzle for directing a jet of air at the skin surface being treated. The elements of FIG. 1 are encased in or mounted to a housing or casing 28 of a size and configuration enabling the pulse generation device to be hand held and easily manipulated for purposes of optically treating different skin surfaces of the individual user.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have a plurality of settings, for instance, high, medium, and low, which vary in the number of applied pulses (e.g., 3, 2, 1), the pulse duration (9 msec, 7 msec, 5 msec), the inter-pulse interval (250 msec, 300 msec, 350 msec), and/or the total energy applied (35 J/cm$^2$, 20 J/cm$^2$, 10 J/cm$^2$). A user could start with a low setting to see, for instance, whether hair reappearance is delayed after hair removal or whether hair stubs are exuded from the skin and if not, try the next higher setting. Usually, it is preferable to use the lowest setting which accomplishes the desired result.

As illustrated in FIG. 1, casing 28 may carry a blade 29 for severing protruding ends of hair fibers along a skin surface. Blade 29 may be a straight edge as in a traditional razor or a cutting edge of an electric shaver. In the latter case, blade 29 is one of plurality of cutting elements movably mounted to casing 28 and operatively connected to a rotary or reciprocating drive element (not illustrated) in the casing.

Figure 2:
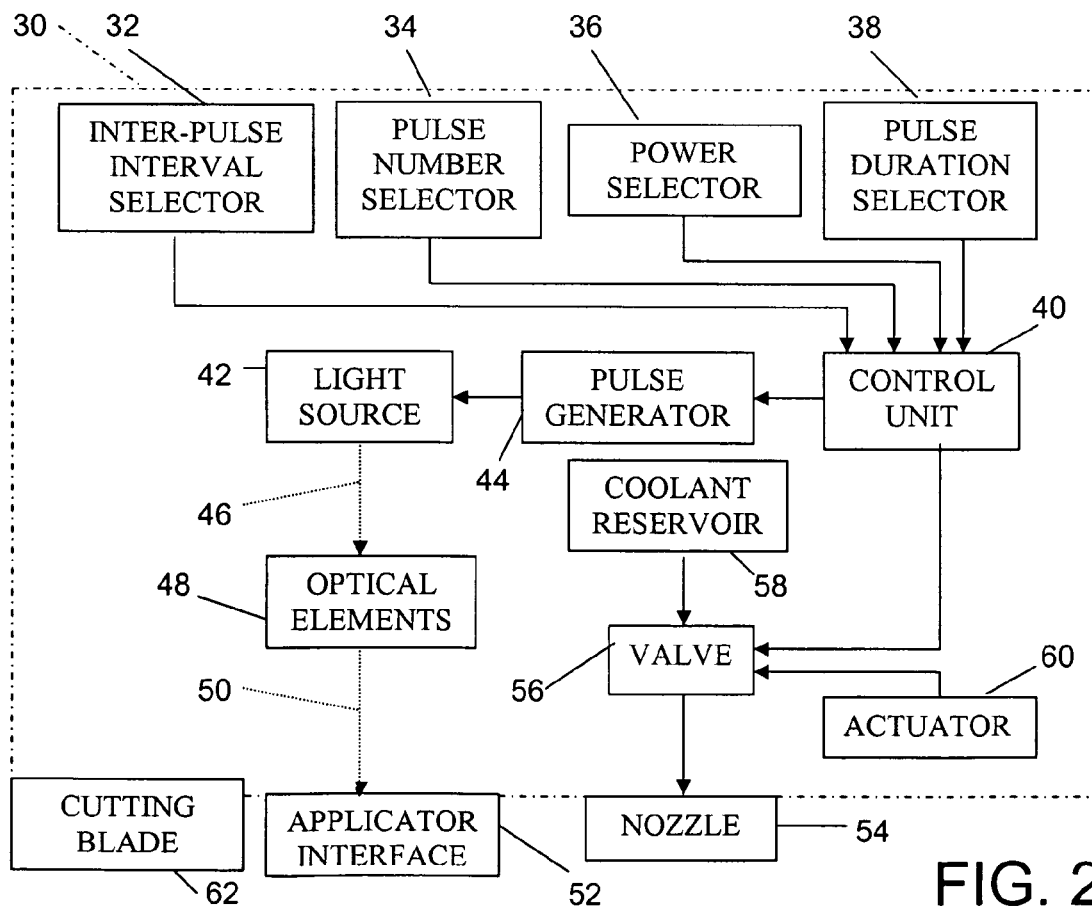
FIG. 2 is a block diagram of another light-pulse generating device for use in a method in accordance with the present invention.

A more advanced or complex device is illustrated in FIG. 2. This device includes a housing or casing 30 having manually actuatable input elements 32, 34, 36, and 38, such as rotary knobs or a solid-state touch screen, which enable a user to individually select multiple operating parameters. Input elements or selectors 32, 34, 36, and 28 are an inter-pulse interval selector, a pulse number selector, a power or energy selector, and a pulse duration selection, respectively. Another selector (not shown) could be for intensity adjustment, while a further selector may be provided for adjusting a light source 42 or a filter in optical elements 48 and/or an applicator 52 for modifying the wavelength band delivered to the target skin surface. Selectors 32, 34, 36, and 38 are operatively tied to a control unit 40 such as a microprocessor or hard-wired log circuit. Control unit 40 regulates the operation of light source 42 such as a conventional flashlamp, either directly or indirectly via a pulse generator 44. Light 46 from source 42 is transmitted along a path through optical elements 48 optionally including one or more reflectors, lenses, and filters (not separately shown). Light 50 at an output of the optical array 48 is applied to a skin surface via applicator or interface element 52. Applicator or interface element 52 may take the form of a crystal block, a flexible plastic element, and/or a transparent or translucent pouch filled with a transparent or translucent fluid such as a gel or a liquid. In the case of the flexible applicator element or the fluid-filled pouch, applicator or interface element 52 conforms at least partially to the changing topography of the skin surface under treatment, thereby facilitating the retention of gel between the applicator or interface 52 and the skin surface. This result decreases the likelihood of overexposed or burned skin and generally provides a more uniform application of light with a uniformity of cooling. Safety is enhanced, while the outcomes to successive procedures become increasingly standardized.

As an alternative to the flexible applicator or fluid-filled pouch, applicator or interface element 52 may include a plurality of independently movable substantially rigid transparent or translucent members (not shown) that collectively define a tissue-engaging surface. These independently movable members may take the form of closely packed pins or plates that are each independently spring biased to an extended position. Pressure of topographical dermal features against the independently movable pins or plates during use of the light-pulse generating device causes the pins or plates to move in opposition to the respective spring bias, to thereby conform the tissue engaging surface of the light-pulse generating device to the skin surface under treatment. The independently movable pins or plates may be disposed in a holder or bracket attached to the housing or casing 30 and retained there by friction forces.

Where applicator 52 (or 26) includes a gel-filled pouch, the pouch (52) may be provided with perforations on a skin-contacting surface for exuding the gel for cooling purposes. Alternatively, as shown in FIG. 2, the light pulse device may be provided with a fluid dispenser such as a spray nozzle 54 connected to a valve 56 downstream of a pressurized coolant reservoir 58. In response to an operation of a manual actuator 60 or in response to signals from control unit 40, valve 56 enables a flow of coolant from reservoir 58 to nozzle 54 for application to a selected skin surface. In the event that applicator or interface element 52 is a bag or pouch, reservoir 58 and valve 56 may be connected to the applicator or interface element for supplying a gel or fluid coolant thereto.

As illustrated in FIG. 2, casing 30 may carry a blade 62 for severing protruding ends of hair fibers along a skin surface. Blade 62 may be a straight edge as in a traditional razor or a cutting edge of an electric shaver. In the latter case, blade 62 is one of plurality of cutting elements movably mounted to casing 30 and operatively connected to a rotary or reciprocating drive element (not illustrated) in the casing.

In one embodiment of the device of FIG. 2, suitable for professional but not home use, inter-pulse interval selector 32 provides for intervals in a range from 1 μsec and 2 seconds, whereas pulse number selector 34 is enabled for pulse sequences of one to ten pulses. In addition, power selector 36 permits treatment energies between one microJoule per square centimeter of skin surface and 200 Joules per square centimeter, while pulse duration selector 38 enables pulses of 1 microsecond (μsec) to 2 seconds in length. Total pulse sequence duration, from the beginning of the first pulse to the termination of the final pulse, ranges from 1 μsec to 38 seconds. The various pulse sequence parameters may be selectable from sets of discrete values or, alternatively, from continuous ranges.

In the device of FIG. 2, the various parameters are typically not completely independent inasmuch as the total energy selected will function as a constraint on the ranges available for the other parameters, that is, the total energy selected will serve to regulate or circumscribe the ranges available to the user for the other pulse sequence parameters. Where the device of FIG. 2 has no intensity adjustment capability, a selection of the total energy and the pulse duration may determine the number of pulses. Similarly, a selection of the total energy and the number of pulses may determine the pulse duration. If the intensity is an adjustable parameter, once the total energy has been chosen, the user will be able to select the magnitudes of two of the three parameters, pulse duration, intensity and number of pulses. The inter-pulse interval is related to the rate at which radiant energy is applied to a skin surface and may accordingly be subjected to some programmed control. Longer pulse durations and/or delays will deliver energy at a slower rate (total energy is distributed over longer time) and therefore be safer to use with higher energy levels. Preferably, the total energy is always a selectable parameter and is best selected prior to the setting of the other parameters. However, the device of FIG. 2 may be preprogrammed to limit the rate at which radiant energy is applied to a skin surface, which will force restrictions on the user's ability to select pulse parameter values.

In an alternative embodiment of the device of FIG. 2, suitable for home use, inter-pulse interval selector 32 enables a selection of intervals ranging from 200 msec to 2 seconds, while power selector 36 enables treatment energies between 1 μJ/cm² and 40 J/cm². Preferably, the pulse duration and the number of pulses available for selection are restricted so as to prevent the user from delivering energy at too high a rate. If the user selects a large pulse number, the pulse duration is necessarily short, whereas a small number of pulses forces a longer pulse duration in order to achieve the selected total energy. It is preferable to use a larger number of pulses and a smaller pulse duration in order to limit the rate at which light energy is applied to a skin surface. Pulse number selector 34 may therefore enable a selection of three to ten pulses per pulse sequence, while pulse duration selector 38 enables a selection of pulses lasting 1 μsec to 10 msec. The various pulse sequence parameters may be selectable from sets of discrete values or, alternatively, from continuous ranges.

A person may use the device of FIG. 1 or 2 to apply pulses of light to a hair-bearing skin surface for purposes of enhancing, facilitating, or improving the results of temporary hair removal by one or more different techniques including shaving, waxing, plucking, using depilatory creams, etc. Where shaving is the technique used, the shaving may be accomplished using blade 29 or 62 to sever protruding hairs at the skin line. In that event, the application of light pulses may be contemporaneous or substantially simultaneous with the cutting of the protruding hairs by blade 29 or 62. Blades 29 and 62 may be omitted from the respective devices of FIGS. 1 and 2, in which case the hair removal is accomplished by an instrumentality separate from the pulsed-light device.

Where the device of FIG. 1 or 2 is used in conjunction with a non-light removal process, the light pulses may be applied before the removal of the protruding hair fibers, but preferably the light pulses are applied to the skin surface substantially during or after the removal of the protruding hair fibers. The absorption of light energy by the remaining (sub-surface) portions of the hair fibers can produce one or more effect that enhances, facilitates, or improves the result of temporary hair removal. Some examples of such effects include (a) rounding-off or blunting the free ends of the remaining (sub-surface) hair portions to prevent ingrown hair, (b) shortening the remaining (sub-surface) portions of the hair fibers to delay the reappearance of the hair along the target skin surface, and (c) thinning the hair shafts (whether protruding or sub-surface) to facilitate subsequent removal of the grown hair.

The present method using the device of FIG. 1 or 2 is preferably implemented without the application of an exogenous chromophore. This simplifies the hair removal process.

In one method utilizing the device of FIG. 1 or 2, a user applies one or more pulses of light energy to a skin surface having protruding hair fibers. Preferably during the same treatment session, which typically lasts under an hour, the user removes the protruding hair fibers from the skin surface by a process different from the application of light energy. This non-light process may be a waxing, shaving, plucking, or tweezing process or a process involving the application of depilatory creams (including gels and other carrier compositions). In some applications, the process for the removal of protruding hairs may alternatively take the form of a lightbased process such as one using laser radiation.

Within a first predetermined time after the applying of the pulses to the skin surface and after the hair portions beneath the skin surface have grown and reappeared as protruding fibers along the skin surface, the user subsequently applies one or more pulses of light to the skin surface in a second treatment session. Necessarily, this second treatment session is temporally spaced by a substantial interval (at least hours, but more typically days) from the first treatment session. During this second treatment session, again typically lasting no more than an hour, the user removes protruding fibers from the skin surface again by a process different from the application of light energy.

It is possible for the protruding hair fibers to be removed from the skin surface in treatment sessions that are different (temporally spaced) from the treatment sessions in which the light pulses are applied. In that case, the removal of the hair is effectuated within a predetermined time after the user applies the respective light pulses to the skin surface. The time interval between light application and removal process may be on the order of a half hour, several hours, or a day or two.

In this method, where the device of FIG. 1 or 2 is used to apply light pulses prior to the removal of hair fibers, the light pulses are characterized by pulse parameters including radiation wavelength such that light of the pulses is absorbed by the hair fibers to at least weaken the hair fibers, thereby facilitating removal of the hair fibers respectively by the first process and the second process.

In a variation of this method for temporarily removing hair, the light application occurs contemporaneously with or after the removal of the hair fibers. Typically, the hair fibers are removed by a non-light process such as a waxing, shaving, plucking, or tweezing process or a process involving the application of depilatory creams (including gels and other carrier compositions). Alternatively, light energy may be used to remove the hair fibers and pulsed incoherent radiation used in a supporting or enhancing role. In any event, the light application is accomplished in the absence of exogenous chromophores. The light wavelength or range of wavelengths is selected to ensure absorption by endogenous chromphores (chiefly melanin) in the hair fibers or shafts.

In this variation of the hair removal method, the user removes protruding hair fibers from a skin surface by a process other than an application of light energy to the skin surface. Thereafter or contemporaneously therewith, and prior to a reappearance of protruding hair on the skin surface, the user applies one or more pulses of light to the skin surface using the device of FIG. 1 or 2. The pulses of light are applied in the absence of an exogenous chromophore on the skin surface and the hair fibers along the skin surface. After the removal of the hair fibers from the skin surface and the application of the light pulses to the skin surface, the user waits for the hair to grow again and protrude along the skin surface. After the reappearance of protruding hair fibers along the skin surface, the user removes the protruding hair fibers again by a process other than an application of light energy to the skin surface. This hair removal process may be the same as that used previously or may be another process, for example, waxing, tweezing, plucking, cutting, shaving, or chemically severing. After the removing of the protruding hair fibers or contemporaneously (or substantially simultaneously) therewith, the user applies one or more pulses of light to the skin surface. The applying of pulses of light is carried out in the absence of an exogenous chromophore on the skin surface and the hair fibers along the skin surface.

Preferably the light is applied to the skin surface during the same treatment session that the protruding hair fibers are removed from the skin surface. Typically, a hair treatment session is carried out during a single sitting or during one visit to the bathroom or a hair treatment salon. Thus, a treatment session as that term is used herein contemplates a collection of activities that are collectively undertaken to accomplish a single cosmetic result, namely, the temporary removal of hairs from a skin surface.

A treatment session as disclosed herein contemplates a primary hair removal process and an ancillary light application. The primary hair removal process is typically chemical or mechanical, rather than photometric. However, one or more forms of light energy, such as laser radiation or pulsed incoherent light, may be used to remove hairs, with one or more additional treatments of light energy, e.g., incoherent light pulses, being used as an enhancing supplement.

Successive hair treatment sessions are temporally spaced from one another by a substantial waiting period. This waiting period is long enough so that the hair has opportunity to grow a perceptible amount between successive treatment sessions. For certain areas of the body, treatment sessions may be spaced by as little as several hours (e.g., 6-12 hours), while for other areas of the body treatment sessions can be spaced by days or even weeks. As elucidated elsewhere herein, the application of the ancillary light pulses (laser or incoherent) may be relied on to lengthen the time between successive treatment sessions.

Hair treatment sessions may vary in duration from a few minutes to about an hour or more, depending on size of the skin area being treated, as well as the number of ancillary treatments (e.g. other than light) performed. Other ancillary treatments may include mechanical manipulation (massage) or the application of chemical compositions such as moisturizers and perfumes. Typically, the treatment sessions are no more than about one hour in length. Of course, longer sessions are possible, particularly in special circumstances such as spa settings.

Where the pulses of an ancillary light treatment as discussed above are applied after hair removal, the pulse parameters include radiation wavelengths such that the pulse light is absorbed by the hair fibers to at least delay a reappearance of the hair fibers on the skin surface. In addition, the pulse parameters may be such that light of the pulses is absorbed by the hair fibers to blunt free ends of remaining portions of the hair fibers, thereby reducing the chances that the hair will subsequently become ingrown.

The light pulse devices of FIGS. 1 and 2 are periodically used to apply pulses of light to a skin surface as an adjunct to removing protruding hair fibers from a skin surface in a plurality of temporally spaced treatment sessions by a process other than an application of light energy. In each of the treatment sessions, one or more light pulses are applied to the skin surface to enhance the removal of hair by the principal process. The pulses are characterized by pulse parameters including radiation wavelength such that light of the pulses is absorbed by the hair fibers below the skin surface. The pulses are applied to the skin surface in the absence of an exogenous chromophore on the skin surface and the hair fibers along the skin surface.

The light pulse devices of FIGS. 1 and 2 (with or without blades 29 and 62) may be used to delay the time that hair is regrown on a skin surface to appear as protruding fibers. In such a method, the device or FIG. 1 or 2 is used on a skin surface where the hair has been removed, before hair reappears on that skin surface. The application of light pulses may maintain the skin surface hair free as long as light pulses are applied prior to the appearance of hair along the skin surface.

In such a method, a user may first perform a calibration or initialization procedure to determine an appropriate pulse setting and a hair-regeneration period for that setting. The term "hair-regeneration period" is used herein to denote the time it takes for hair to reappear on the skin surface after a pulse sequence has been applied to that surface at a selected setting. The following discussion is directed in principal part to the use of pulsed light to remove hair and to delay hair reappearance.

The calibration techniques as discussed herein determine a minimal energy (and possibly other light-pulse parameters) for the removal of hair from a skin surface solely or mainly by the application of light. Where the device of FIG. 1 or 2 is used to enhance hair removal that is accomplished by another process, the same settings are used to affect hair fibers that are below the skin surface.

During the calibration or initialization stage, the user should first select a low-energy pulse sequence to determine whether that sequence is effective in removing the hair of a selected skin region. The individual may find that a given setting does not adequately remove the hair (e.g., some hairs do not fall out) or requires a too frequent treatment. In such cases, the individual should retry the calibration or initialization procedure using a higher-energy setting.

Using the device of FIG. 1, an individual will first select a low setting to determine whether that low setting is effective in hair removal. If not, a next higher or medium setting may be tried. Generally, higher settings will be used only as the circumstances warrant, for instance, if the hair fibers are thick and the skin is light.

In determining optimal settings with the device of FIG. 2, a user should choose initial parameter values which in combination result in the application of small amounts of energy. Thus, where one or more selected pulse parameters are associated with high treatment energies, other pulse parameters should be selected that are associated with low treatment energies.

Where all the pulse parameters are independently adjustable, lower treatment energies will generally result from settings involving few pulses (say, 1-3 instead of 8-10 pulses), long inter-pulse intervals (300 msec or more), short pulse durations (20 msec or less), low light intensity (if selectable, for example, via an adjustable neutral density filter), and low total energies (less than 40 Joules per square centimeter of skin surface). If a given setting proves to be ineffective, the user might adjust selector 32 or 38 to decrease the inter-pulse interval or increase the pulse length, thereby effectively increasing the power or rate at which the radiant energy is delivered to the target skin surface. Alternatively or additionally, the user might increase the number of pulses via selector 34 or increase the applied energy via selector 36. These adjustments will result in an increase in the rate of applied energy if the total time of the pulse sequence is limited. If the light intensity is separately adjustable, one may increase the power or rate of energy delivery by simply selecting a higher intensity value.

Where the various pulse parameters are not independently selectable, for instance, where the total energy applied is a controlling factor, adjustments made in the parameters for purposes of incrementally enhancing the effectiveness of the device of FIG. 2 will be different from the case of completely independent parameter values. For instance, once the total applied energy and total pulse sequence time have been selected, decreasing the number of pulses will require an increase in pulse length and/or an increase in pulse intensity in order to deliver the same amount of total energy in the fixed time. These changes will increase the effectiveness of the light application inasmuch as the rate of energy delivery is increased. In contrast, once the total applied energy and total pulse sequence time have been selected, increasing the pulse duration will decrease the instantaneous rate at which energy is applied to the target skin surface by decreasing the light intensity.

During the calibration or initialization stage of a hair removal method using the device of FIG. 1 or FIG. 2, light is used on skin surfaces with visible and protruding hair. Light is applied to the skin surface and the hair and is directed downward towards the base or bulb of the hair. Immediate damage to the hair may be noted but is not essential. Hairs may fall out during the course of the following month. Hair loss may be gradual or abrupt. No assistance is usually needed in this process.

Since hair growth rates vary from person to person and for different body locations on the same person, users may wish to note the interval between the first treatment and the reappearance of new hair on each skin area.

Because different skin areas have different grades of hair (different colors, different fiber diameters, different hair densities) and different skin pigmentation, etc., different pulse parameter settings are recommended for different skin areas. For example, different settings will be necessary for the underarms and the legs in order to optimize results. In addition, treatment session schedules may also vary from one skin area to another.

After the user has determined appropriate settings of the pulse sequence parameters for different skin areas, the user applies light with those settings as ancillary to hair removal by another, typically non-light-based method. The settings are generally effective to enhance the hair removal process, for example, by destroying hair shafts below the skin surface to delay the time that hair reappears on the skin surface, thereby reducing the number of hair removal sessions per month.

Where pulsed light is applied by itself prior to hair reappearance to further length the interval between successive sessions of removing protruding hair fibers, the user may determines a regeneration period and thus a time that hair is expected to be visible again on the skin surface after the application of pulsed light energy. The user treats each skin surface with pulsed light at the respective settings and at a periodicity set by the respective hair-regeneration period. Successive applications of pulsed light follow at intervals smaller than the detected hair-regeneration period. For instance, if it is determined that hair reappears on a leg at three weeks after treatment with light at a given pulse sequence setting, then light energy at that setting is applied to the leg at, say, two week intervals to maintain the leg free of visible hair. The regeneration period may be measured again after any number of treatments. And if the user finds that the regeneration time has changed, the interval between successive treatment sessions may be adjusted accordingly.

In any event, using pulsed light as an ancillary technique generally reduces the number of hair treatment sessions where a primary hair removal method is used. In addition, where pulsed light energy is applied by itself prior to hair reappearance, determining a hair regeneration period may enable a reduction in the number of pulsed-light hair treatment sessions between the primary hair removal sessions.

The present hair removal method contemplates, therefore, the periodic application to a selected skin surface of a pulse sequence having a predetermined number of pulses of light of a predetermined electromagnetic spectrum, a predetermined duration, a predetermined inter-pulse interval, and a predetermined total energy. These pulse sequence parameters are determined in part by the design of the light generating device used and in part by the selections made by the user. The light treatment temporarily delays a growth of hair through the selected skin surface for the respective hair-regeneration period.

The light of the pulses is generally incoherent and the spectrum includes wavelengths between about 300 nm and 1200 nm. However, single wavelengths of laser or coherent light may be delivered at one time, when desired. Higher wavelengths are used for darker skin, for deeper hairs and deeper removal. In order to limit the depth of penetration of the light, and accordingly the length of the hair-regeneration or hair-regrowth period, the spectrum of the pulses may be limited to shorter wavelengths and may include wavelengths, for instance, below 550 nm.

The light applied to a skin surface by the devices of FIGS. 1 and 2 includes at least one wavelength absorbable by an endogenous chromophore in a person's hair. The endogenous chromophore may be a form of melanin such as pheomelanin or eumelanin. In a more advanced embodiment the light application device may include a setting or control (not shown) for selecting a spectrum or range of wavelengths appropriate to the user's hair color. For instance, for lighter hair, the wavelengths selected encompass one or more natural absorption wavelengths of pheomelanin. For darker hair, the wavelengths selected encompass one or more natural absorption wavelengths of eumelanin. In any event, the devices of FIGS. 1 and 2 are used without the application of an exogenous chromophore to a target skin surface for light absorption purposes. Hair removal and growth retardation are accomplished by light absorption solely by one or more endogenous chromophores.

In other embodiments of a light generation and application device for hair treatment, one or more of the pulse parameters may vary during a single treatment session. For instance, the inter-pulse interval or the pulse duration may increase or decrease from the beginning of a pulse sequence to the end of the pulse sequence. The resulting instantaneous rate of energy application may therefore vary during the pulse sequence.

Listed below are a number of exemplary settings or combinations of operational parameters particularly suitable for home use and attainable with either the device of FIG. 1 having pre-established settings or parameter combinations or the device of FIG. 2 where the various pulse sequence parameters may be individually adjusted independently of the other parameters. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings. These settings may be used to deliver light to a skin surface as an adjunct or ancillary to the removal of hair by a non-light process. In that case, the light is preferably applied to the skin surface during a hair treatment session wherein protruding fibers or shafts are removed by a method other than light application such as waxing, shaving, tweezing, plucking, or depilating with a cream or gel.

Home Use Example 1. In a preferred setting or combination of operational parameters suitable for home use, an incoherent light applicator device for temporary hair removal or ancillary hair treatment generates pulses with a pulse number of two, a pulse duration of 7 msec, an inter-pulse interval of 300 msec, a total pulse energy of 10 $J/cm^2$, and a spectral distribution of a commercially available flashlamp, including wavelengths between 500 and 1200 nm.

Home Use Example 2. A slightly higher setting or combination of operational parameters for an incoherent light applicator device suitable for home use involves a pulse sequence with a pulse number of two, a pulse duration of 7 msec, an inter-pulse interval of 250 msec, a total pulse energy of 10 $J/cm^2$, and a spectral distribution of a commercially available flashlamp, including wavelengths between 500 and 1200 nm. Although the total amount of energy is the same as in the first example, the shorter interpulse interval means that the rate of energy transmission to the target skin surface is higher.

Home Use Example 3. A higher setting or combination of operational parameters for an incoherent light applicator device involves pulses with a pulse number of two, a pulse duration of 5 msec, an inter-pulse interval of 250 msec, a total pulse energy of 12 $J/cm^2$, and a spectral distribution of a commercially available flashlamp, including wavelengths between 500 and 1200 nm. In this example, not only is the total energy larger than in the second example, but the rate of energy application is higher owing to the shorter pulse duration.

Home Use Example 4. An even higher setting or combination of operational parameters for an incoherent light applicator device involves pulses with a pulse number of two, a pulse duration of 5 msec, an inter-pulse interval of 210 msec, a total pulse energy of 18 $J/cm^2$, and a spectral distribution of a commercially available flashlamp, including wavelengths between 500 and 1200 nm. The pulse sequence of this example delivers radiant energy at a higher rate than in the third example because of the shorter inter-pulse interval and the slightly higher energy delivered per pulse.

Home Use Example 5. In a low setting or combination of operational parameters, an incoherent light applicator device produces pulses with a pulse number of two, a pulse duration of 5 msec, an inter-pulse interval of 350 msec, a total pulse energy of 7 $J/cm^2$, and a spectral distribution of a commercially available flashlamp, including wavelengths between 500 and 1200 nm. The pulse sequence of this example delivers a small amount of energy, at a low rate (e.g., long inter-pulse interval).

Home Use Example 6. A slightly higher setting or combination of operational parameters for an incoherent light applicator device involves pulses with a pulse number of two, a pulse duration of 5 msec, an inter-pulse interval of 300 msec, a total pulse energy of 10 $J/cm^2$, and a spectral distribution of a commercially available flashlamp, including wavelengths between 500 and 1200 nm.

Home Use Example 7. A lower setting or combination of operational parameters for an incoherent light applicator device involves pulses with a pulse number of three, a pulse duration of 5 msec, an inter-pulse interval of 300 msec, a total pulse energy of 10 $J/cm^2$, and a spectral distribution of a commercially available flashlamp, including wavelengths between 500 and 1200 nm.

Home Use Example 8. Another setting or combination of operational parameters for an incoherent light applicator device involves pulses with a pulse number of two, a pulse duration of 7 msec, an inter-pulse interval of 250 msec, a total pulse energy of 10 $J/cm^2$, and a spectral distribution of a commercially available flashlamp, including wavelengths between 500 and 1200 nm.

The devices of FIGS. 1 and 2 may be provided with a band-pass filter for limiting the spectral distribution of the generated light pulses to wavelengths in a given band, for instance, between 700 nm and 900 nm. Alternatively, a low-pass filter may be used for transmitting to a skin surface only wavelengths less than a predetermined maximum, such as 900 nm, 750 nm, or 550 nm. The lower the wavelength the less likely the light will penetrate deeply and damage cellular and histological elements as deep as the bulb parts of the hair follicles. Shorter wavelengths, for instance, below 550 nm are useful for limiting the depth of penetration. It is to be understood, however, that the less the depth of penetration, the shorter the time between successive applications of light energy necessary to maintain a hair free skin surface. Thus, instead of a month or a week, the time between successive hair removal procedures might be as little as one or two days.

Depth of penetration may also be limited by using lower light intensities. Neutral density or "gray" filters may be used to reduce the intensity of the light applied to the selected skin surfaces.

Listed below are a number of exemplary settings or combinations of operational parameters particularly suitable for professional devices. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings. These settings may be used to deliver light to a skin surface as an adjunct or ancillary to the removal of hair by a non-light process. In that case, the light is preferably applied to the skin surface during a hair treatment session wherein protruding fibers or shafts are removed by a method other than light application such as waxing, shaving, tweezing, plucking, or depilating with a cream or gel.

Professional Use Example 1. In a setting or combination of operational parameters suitable for professional use, an incoherent light applicator device for temporary hair removal or ancillary hair treatment generates pulses with a pulse number of two, a pulse duration of 7 msec, an inter-pulse interval of 150 msec, a total pulse energy of 30 J/cm$^2$, and a spectral distribution of a commercially available flashlamp, including wavelengths between 500 and 1200 nm.

Professional Use Example 2. A slightly higher setting or combination of operational parameters for an incoherent light applicator device involves pulses with a pulse number of two, a pulse duration of 7 msec, an inter-pulse interval of 100 msec, a total pulse energy of 30 J/cm$^2$, and a spectral distribution of a commercially available flashlamp, including wavelengths between 500 and 1200 nm.

Professional Use Example 3. A lower setting or combination of operational parameters for an incoherent light applicator device involves pulses with a pulse number of two, a pulse duration of 9 msec, an inter-pulse interval of 100 msec, a total pulse energy of 30 J/cm$^2$, and a spectral distribution of a commercially available flashlamp, including wavelengths between 500 and 1200 nm.

Professional Use Example 4. A higher setting or combination of operational parameters for an incoherent light applicator device involves pulses with a pulse number of two, a pulse duration of 9 msec, an inter-pulse interval of 100 msec, a total pulse energy of 50 J/cm$^2$, and a spectral distribution of a commercially available flashlamp, including wavelengths between 500 and 1200 nm.

Professional Use Example 5. In a relatively low setting or combination of operational parameters for professional use, an incoherent light applicator device produces pulses with a pulse number of two, a pulse duration of 9 msec, an inter-pulse interval of 200 msec, a total pulse energy of 20 J/cm$^2$, and a spectral distribution of a commercially available flashlamp, including wavelengths between 500 and 1200 nm.

Professional Use Example 6. A slightly higher setting or combination of operational parameters for an incoherent light applicator device involves pulses with a pulse number of two, a pulse duration of 5 msec, an inter-pulse interval of 150 msec, a total pulse energy of 20 J/cm$^2$, and a spectral distribution of a commercially available flashlamp, including wavelengths between 500 and 1200 nm.

Professional Use Example 7. Another higher setting or combination of operational parameters for an incoherent light applicator device involves pulses with a pulse number of two, a pulse duration of 5 msec, an inter-pulse interval of 150 msec, a total pulse energy of 25 J/cm$^2$, and a spectral distribution of a commercially available flashlamp, including wavelengths between 500 and 1200 nm.

An incoherent light applicator device for professional use may also be provided with a band-pass filter for limiting the spectral distribution of the generated light pulses to wavelengths in a given band, for instance, between 700 nm and 900 nm. Again, a low-pass filter may be used for transmitting to a skin surface only wavelengths less than a predetermined maximum, such as 900 nm, 750 nm, or 550 nm.

The hair treatment method using the light device or FIG. 1 or 2 to delay the appearance of hair on a smooth skin surface, whether as a primary or an ancillary treatment, contemplates not only temporary hair removal at an optically treated skin surface, but also retarding the growth of hair fibers located at or along that skin surface. By counting the days to hair reappearance after several hair depilation procedures over a course of a few months, it is possible to determine a reduction in hair growth rate owing to the application of electromagnetic radiation. A user who starts using the light application process at one inter-application interval may subsequently use a longer inter-application interval and still maintain a hair-free skin surface. Of course, the degree of hair growth rate reduction will vary from person to person and even from skin location to skin location on the same person. For example, two users initially required to apply the pulsed light energy at intervals of one week in order to prevent the reappearance of hair on the treated hair surface may find that after several months one user need reapply light energy only every two weeks and the other user need reapply light energy only every month.

It is to be noted that the hair treatment method described herein contemplates possibly multiple passes over any particular skin surface. The selected light treatment parameters may be the same for each pass or may vary from pass to pass. In addition, the passes may follow immediately after one another or may be spaced by an interval during which, for instance, the light treatment device is used to apply light pulses to another area of the user's skin. An advantage of multiple passes is that the total power applied to a given skin surface may be reduced relative to that needed for accomplishing the desired hair removal by a single pass or light treatment. For example, instead of a single pass of 50 Joules/cm$^2$, hair could be effectively removed temporarily by two passes of 20 Joules/cm$^2$ apiece.

Although the invention has been described in terms of particular embodiments and applications, one of ordinary skill in the art, in light of this teaching, can generate additional embodiments and modifications without departing from the spirit of or exceeding the scope of the claimed invention. For example, light sources 18 and 42 may take the form of laser sources. In that case, if optical elements 22 and 48 include any filters, those filters are neutral density filters for reducing the intensity of the transmitted radiation. Where light sources 18 and 42 are tunable laser sources, then an additional actuator may be provided for frequency selection purposes.

The present disclosure is directed primarily to temporary hair removal methods. However, the same techniques may be applied where the intent is permanent hair removal, but the removal processes are effectuated on multiple occasions or treatment sessions, owing to failure of the processes to remove all hair from a target skin surface.

Accordingly, it is to be understood that the drawings and descriptions herein are proffered by way of example to facilitate comprehension of the invention and should not be construed to limit the scope thereof.

What is claimed is:

1. A hair removal method comprising:
  applying one or more first pulses of radiant energy to a skin surface having protruding hair fibers;
  within a first predetermined time after the applying of the pulses to said skin surface and within the same hair removal session applying of said pulses to said skin surface, removing the protruding hair fibers from said skin surface by a first process different from the application of radiant energy, said first pulses being characterized by pulse parameters including radiation wavelength such that energy of said first pulses is absorbed by the hair fibers and thereby changes one or more physical characteristics of the hair fibers to enhance or facilitate temporary removal of protruding hair fibers along said skin surface by said first process, substantially all of the removed hair fibers eventually reappearing on said skin surface;

subsequently, after the hair portions beneath said skin surface have grown and reappeared as protruding fibers along said skin surface, applying one or more second pulses of radiant energy to said skin surface; and within a second predetermined time after the applying of said second pulses of radiant energy to said skin surface and within the same hair removal session as the applying of said second pulses to said skin surface, removing the protruding fibers from said skin surface by a second process different from the application of radiant energy, said second pulses being characterized by pulse parameters including radiation wavelength such that energy of said second pulses is absorbed by the hair fibers and thereby changes one or more physical characteristics of the hair fibers to enhance or facilitate removal of protruding hair fibers along said skin surface by said second process, substantially all of the removed hair fibers eventually reappearing on said skin surface.

2. The method defined in claim 1 wherein the applying of said first pulses of radiant energy is carried out during a first hair treatment session and the applying of said second pulses of radiant energy is carried during a second treatment session temporally spaced from said first treatment session, the removing of protruding hair fibers by said first process taking place during said first treatment session and the removing of protruding hair fibers by said second process taking place during said second treatment session.

3. The method defined in claim 2 wherein protruding hairs fibers are removed during said first treatment session within about one hour of the applying of said first pulses of radiant energy to said skin surface, protruding hair fibers being removed during said second treatment session within about one hour of the applying of said second pulses of radiant energy.

4. The method defined in claim 1 wherein said first process and said second process different from the application of radiant energy are each taken from the group consisting of waxing, shaving, plucking, tweezing, and using depilatory creams.

5. The method defined in claim 1 wherein said first pulses and said second pulses are characterized by pulse parameters including radiation wavelength such that radiant energy of said first pulses and said second pulses is absorbed by the hair fibers to at least weaken the hair fibers, thereby facilitating removal of the hair fibers respectively by said first process and said second process.

6. The method defined in claim 1 wherein said first process and said second process are the same type of process.

7. The method defined in claim 1 wherein the applying of said first pulses and the applying of said second pulses are carried out in the absence of an exogenous chromophore on the skin surface or in or surrounding the hair fibers at or below the skin surface.

8. A temporary hair removal method comprising:
removing protruding hair fibers from a skin surface by a first process other than an application of radiant energy to said skin surface;

contemporaneously with or after the removing of the protruding hair fibers, and prior to a reappearance of protruding hair on said skin surface, applying one or more first pulses of radiant energy to said skin surface, the applying of said pulses of radiant energy being carried out in the absence of an exogenous chromophore on the skin surface or in or surrounding the hair fibers at or below the skin surface, the removing of protruding hair fibers and the applying of said pulses of radiant energy resulting in a temporary removal of substantially all of the protruding hairs along said skin surface, so that substantially all of the removed hair fibers eventually reappear on said skin surface;

after the applying of said first pulses to said skin surface and after a reappearance of protruding hair fibers along said skin surface, removing the protruding hair fibers from said skin surface by a second process other than an application of radiant energy to said skin surface; and contemporaneously with or after the removing of the protruding hair fibers by said second process, applying one or more second pulses of radiant energy to said skin surface, the applying of said second pulses of radiant energy being carried out in the absence of an exogenous chromophore on said skin surface and the hair fibers along said skin surface, the removing of protruding hair fibers by said second process and the applying of said second pulses of radiant energy resulting in a temporary removal of substantially all of the protruding hairs along said skin surface, so that substantially all of the removed hair fibers eventually reappear on said skin surface, said first pulses of radiant energy being characterized by pulse parameters including radiation wavelength such that radiant energy of said first pulses is absorbed by the hair fibers and thereby temporarily changes one or more physical characteristics of the hair to enhance or facilitate the removal of protruding hair along said skin surface by at least said second process.

9. The method defined in claim 8 wherein the applying of said first pulses of radiant energy is carried out during a first hair treatment session and the applying of said second pulses of radiant energy is carried during a second treatment session temporally spaced from said first treatment session, the removing of protruding hair fibers by said first process taking place during said first treatment session and the removing of protruding hair fibers by said second process taking place during said second treatment session.

10. The method defined in claim 9 wherein the applying of said first pulses of radiant energy to said skin surface occurs within about one hour of the removing of protruding hairs fibers by said first process, the applying of said second pulses of radiant energy to said skin surface occurring within about one hour of the removing of protruding hairs fibers by said second process.

11. The method defined in claim 8 wherein said first process and said second process are each taken from the group consisting of waxing, shaving, plucking, tweezing, and using depilatory creams.

12. The method defined in claim 8 wherein said first pulses and said second pulses are characterized by pulse parameters including radiation wavelength such that radiant energy of said first pulses and said second pulses is absorbed by the hair fibers to at least delay a reappearance of the hair fibers on said skin surface.

13. The method defined in claim 8 wherein said first pulses and said second pulses are characterized by pulse parameters including radiation wavelength such that radiant energy of said first pulses and said second pulses is absorbed by the hair fibers to blunt free ends of remaining portions of the hair fibers, thereby reducing the chances that the hair will subsequently become ingrown.

14. The method defined in claim 8 wherein said first process and said second process are the same type of process.

15. A method for temporarily removing hair from a skin surface, comprising:

in each of a plurality of temporally spaced treatment sessions, removing protruding hair fibers from the skin surface at least in part by a process other than an application of radiant energy, the removing of the protruding hair fibers being effectuated so that substantially all of the hair fibers along said skin surface regrow and reappear after each of said treatment sessions; and in each of said treatment sessions applying one or more radiant energy pulses to said skin surface to change a physical characteristic of the hair so as to enhance or facilitate the removal of hair by said process, said pulses being characterized by pulse parameters including radiation wavelength such that radiant energy of said pulses is absorbed by the hair fibers below said skin surface so that substantially all of the hair fibers along said skin surface regrow and reappear after each of said treatment sessions, the applying of said pulses being carried out in the absence of an exogenous chromophore on the skin surface or in or surrounding the hair fibers at or below the skin surface.

16. A method for temporarily removing hair from a skin surface, comprising:

in each of a plurality of temporally spaced treatment sessions, removing substantially all protruding hair fibers from the skin surface at least in part by an application of radiant energy to said skin surface in the absence of an exogenous chromophore, the removing of the protruding hair fibers being effectuated so that substantially all of the hair fibers along said skin surface regrow and reappear after each of said treatment sessions; and in each of said treatment sessions applying one or more pulses of radiant energy to said skin surface to enhance the removal of hair by the radiant energy, said pulses being characterized by pulse parameters including radiation wavelength such that radiant energy of said pulses is absorbed by the hair fibers below said skin surface and thereby changes one or more physical characteristics of the hair to enhance or facilitate removal of protruding hair along said skin surface said pulses being selected such that substantially all of the hair fibers along said skin surface regrow and reappear after each of said treatment sessions.

17. A method for temporarily removing hair from a skin surface, comprising:

in each of a plurality of temporally spaced treatment sessions, removing protruding hair fibers from the skin surface in part by an application of radiant energy and in part by a process other than the application of radiant energy, the removing of the protruding hair fibers being effectuated so that substantially all of the hair fibers along said skin surface regrow and reappear after each of said treatment sessions; and within a predetermined time interval of each of said treatment sessions, applying one or more pulses of radiant energy to said skin surface to enhance the removal of hair by the radiant energy and the process other than the application of radiant energy, said pulses being characterized by pulse parameters including radiation wavelength such that radiant energy of said pulses is absorbed by the hair fibers below said skin surface and thereby changes one or more physical characteristics of the hair to enhance or facilitate removal of protruding hair along said skin surface.

18. The method defined in claim 17 wherein the removing of protruding hair fibers in one or more of said treatment sessions is accomplished in part by an application of radiant energy and in part by a non-light process different from processes used in other of said treatment sessions.

* * * * *